(12) United States Patent
Wang et al.

(10) Patent No.: US 7,004,963 B2
(45) Date of Patent: Feb. 28, 2006

(54) CONFORMABLE BALLOONS

(75) Inventors: Yiqun Bruce Wang, Maple Grove, MN (US); John Jianhua Chen, Plymouth, MN (US); Lixiao Wang, Long Lake, MN (US); Jason Todd Lenz, Maplewood, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 355 days.

(21) Appl. No.: 09/952,397

(22) Filed: Sep. 14, 2001

(65) Prior Publication Data

US 2003/0055378 A1 Mar. 20, 2003

(51) Int. Cl.
*A61M 29/00* (2006.01)

(52) U.S. Cl. ..................... 623/1.11; 606/192
(58) Field of Classification Search ......... 606/191–194; 623/1.11; 604/103.06–103.09, 103.01–103.03
See application file for complete search history.

(56) References Cited

U.S. PATENT DOCUMENTS

| | | | |
|---|---|---|---|
| 2,833,706 A | 5/1958 | Janacek ................... 604/96 |
| 4,105,732 A | 8/1978 | Slingluff .................. 264/104 |
| 5,248,305 A | 9/1993 | Zdrahala .................. 604/280 |
| 5,363,318 A | 11/1994 | McCauley | |
| 5,423,745 A | 6/1995 | Todd et al. ................ 604/53 |
| 5,443,907 A | 8/1995 | Slaikeu et al. ............. 428/375 |
| 5,534,007 A | 7/1996 | St. Germain et al. ....... 606/108 |
| 5,545,132 A | 8/1996 | Fagan et al. ............... 604/96 |
| 5,620,457 A | 4/1997 | Pinchasik et al. .......... 606/194 |
| 5,645,560 A * | 7/1997 | Crocker et al. ............ 606/192 |
| 5,653,691 A | 8/1997 | Rupp et al. ................ 604/96 |
| 5,702,364 A | 12/1997 | Euteneuer et al. .......... 604/96 |
| 5,702,418 A | 12/1997 | Ravenscroft ............... 606/198 |
| 5,792,300 A | 8/1998 | Inderbitzen et al. ........ 156/244 |
| 5,797,877 A | 8/1998 | Hamilton et al. ........... 604/96 |
| 5,879,369 A | 3/1999 | Ishida ...................... 606/194 |
| 5,897,239 A | 4/1999 | Caruthers, Jr. et al. | |
| 5,913,871 A * | 6/1999 | Werneth et al. ............ 623/1.11 |
| 5,944,726 A | 8/1999 | Blaeser et al. ............. 606/108 |
| 5,954,740 A | 9/1999 | Ravenscroft et al. ....... 606/194 |
| 5,957,930 A | 9/1999 | Vrba ....................... 606/108 |
| 5,968,069 A | 10/1999 | Dusbabek et al. .......... 606/194 |
| 5,980,532 A | 11/1999 | Wang ...................... 606/108 |
| 5,980,533 A | 11/1999 | Holman .................... 606/108 |
| 6,007,543 A | 12/1999 | Ellis et al. ................ 606/108 |
| 6,013,728 A | 1/2000 | Chen et al. ................ 525/92 |
| 6,022,359 A | 2/2000 | Frantzen ................... 606/108 |
| 6,024,722 A | 2/2000 | Rau et al. .................. 604/96 |
| 6,036,697 A | 3/2000 | DiCaprio .................. 606/108 |
| 6,068,634 A | 5/2000 | Lorentzen Cornelius et al. ........................ 606/108 |
| 6,096,056 A | 8/2000 | Brown ..................... 606/194 |
| 6,110,192 A | 8/2000 | Ravenscroft et al. ....... 606/194 |
| 6,129,706 A | 10/2000 | Janacek .................... 604/96 |
| 6,146,356 A | 11/2000 | Wang et al. ............... 604/96 |
| 6,193,738 B1 | 2/2001 | Tomaschko et al. ........ 606/194 |
| 6,306,162 B1 * | 10/2001 | Patel ...................... 623/1.11 |

FOREIGN PATENT DOCUMENTS

| | | |
|---|---|---|
| EP | 1 008 363 A2 | 6/2000 |
| FR | 2 753 907 | 10/1996 |
| WO | WO 99/10037 | 3/1999 |

* cited by examiner

*Primary Examiner*—Tan-Uyen T. Ho
(74) *Attorney, Agent, or Firm*—Vidas, Arrett & Steinkraus PA

(57) ABSTRACT

An inflatable medical balloon for multiple procedures, including angioplasty procedures, procedures for delivering medical devices, such as stents, and a method of making the catheter systems. The catheter system employs a balloon having a plurality of flexible portions and a combination of hard and soft portions.

16 Claims, 5 Drawing Sheets

CONFORMABLE BALLOONS

FIELD OF THE INVENTION

This invention relates to catheters used for multiple procedures, including angioplasty procedures, procedures for delivering medical devices, such as stents, and a method of making the catheter systems. The catheter system employs a balloon having a plurality of flexible portions and a combination of hard and soft portions.

BACKGROUND OF THE INVENTION

Catheters are used for many medical purposes. The present invention is not directed to a specific type of catheter, but rather types of balloons and methods of making said balloons. The balloons may be used for a variety procedures, such as, but not limited to, plain old balloon angioplasty (POBA), stent delivery, peripheral catheter procedures.

Examples of catheters and procedures are addressed below for the sake of background.

In typical PTA or PTCA procedures, a guiding catheter is percutaneously introduced into the cardiovascular system of a patient and advanced through the aorta until the distal end is in the desired (coronary) artery. Using fluoroscopy, a guide wire is then advanced through the guiding catheter and across the site to be treated in the coronary artery. An over the wire (OTW) balloon catheter is advanced over the guide wire to the treatment site. The balloon is then expanded to reopen the artery. The OTW catheter may have a guide wire lumen which is as long as the catheter or it may be a rapid exchange catheter wherein the guide wire lumen is substantially shorter than the catheter. Alternatively, a fixed wire balloon may be used. This device features a guide wire which is affixed to the catheter and cannot be removed.

To help prevent arterial closure, repair dissection, or prevent restenosis, a physician can implant an intravascular prosthesis, or a stent, for maintaining vascular patency inside an artery or other vessel at the lesion.

Stents are also used for a variety of other purposes including maintaining the patency of any physiological conduit including arteries, veins, vessels, the biliary tree, the urinary tract, the alimentary tract, the tracheobronchial tree, the genitourinary system, and the cerebral aqueduct.

The stent may either be self-expanding or balloon expandable. For the latter type, the stent is often delivered on a balloon and the balloon is used to expand the stent. The self-expanding stents may be made of shape memory materials such as nitinol or constructed of conventional metals but of a design which exhibits self expansion characteristics.

A balloon may be used to widen a vessel into which the catheter is inserted by dilating the blocked vessel, such as in an angioplasty procedure. The catheter may also be used to deliver a medical device, such as a stent, into a body lumen. Some examples of stent delivery balloons are disclosed in U.S. Pat. Nos. 5,702,418, 5,968,069 and 5,797,877, the entire contents of these patents are hereby incorporated by reference.

In these and other medical device delivery applications, radial expansion of a balloon may be used to expand or inflate a stent at a desired positioned within the body. Using a balloon equipped catheter to deliver a stent often requires precise positioning of the balloon and stent as well as a balloon with accurate and predictable expansion properties. The present invention aids in positioning the balloon and stent in the targeted areas with enhanced precision.

Currently, a specific concern physicians have with regard to the difficulty in delivering a stent to the targeted site is vessel straitening. This phenomenon is a result of rigidity built up due to the overlapping of the stent, balloon and typically the inner shaft. To reduce this rigidity, flexible stents have been produced. The present invention, in one aspect, seeks to provide balloons which address this problem, among others.

All US patents and applications and all other published documents mentioned anywhere in this application are incorporated herein by reference in their entirety.

Without limiting the scope of the invention a brief summary of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is directed generally to medical balloon designs which have increased longitudinal flexibility in both the wrapped, collapsed state, while maintaining control of radial expansion. The flexibility is enhanced by creating a plurality of hinge points in the balloon material. These hinge points may be created in a number of ways. The hinge points may be changes in the thickness in the balloon, interruptions in the continuity of the balloon material and/or changes in the physical properties of portions of the balloon. These differing embodiments are discussed in the Detailed Description of the present disclosure.

The balloon designs utilize surface finishing and structure of a balloon body to obtain improved flexibility. The designs work by interrupting the usual straight rigid wall of a standard balloon. In addition, certain aspects of the invention have the potential for improved stent retention due to higher friction between the balloon and stent and a more receptive contour on the surface of the balloon for receiving the stent.

In some aspects, the present invention improves flexibility and also provides for low compliance. Discussions of compliance characteristics may be found in U.S. Pat. Nos. 6,146,356 and 5,980,532.

The invention also contemplates balloons utilizing two materials with different modulus of elasticity. The materials are combined on a balloon in a way as to provide flexibility in the longitudinal direction and stiffness or non-compliance in the radial direction.

A further aspect of the invention contemplates the aid the present designs provide in re-wrap of the balloon. Balloons on catheters may be inflated and deflated by applying internal pressure. To minimize the profile of the catheter, balloons are typically "folded". After the balloon is inflated during use, it is subsequently deflated. It is desired that the balloon be constructed to "re-wrap" into its original configuration upon deflation to maintain the catheter's low profile during withdrawal of the catheter. This re-wrap may be achieved my incorporating a "memory" within the balloon such that when the internal pressure is removed, the balloon tends to return to its original configuration. The present novel designs aid in this re-wrap phenomenon.

Additional details and/or embodiments of the invention are discussed below.

BRIEF DESCRIPTION OF THE SEVERAL VIEWS OF THE DRAWINGS

A detailed description of the invention is hereinafter described with specific reference being made to the drawings in which.

DETAILED DESCRIPTION OF THE INVENTION

Figure 1:
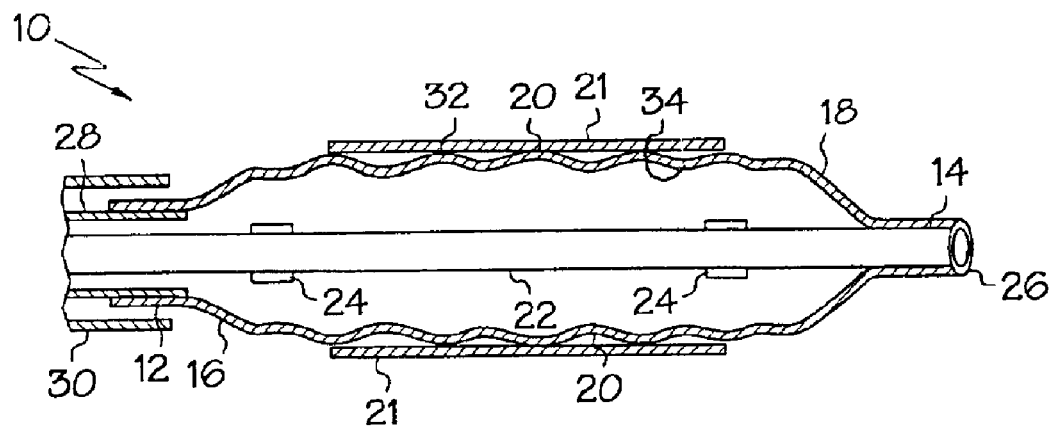
FIG. 1 is a cross-sectional view of the distal end of a balloon catheter illustrating a particular embodiment of the inventive balloon.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, unless otherwise indicated, identical reference numerals used in different figures refer to the same component.

The balloons shown in the figures are partially expanded to illustrate the inventive aspects.

For the purposes of this disclosure, the term stent refers to stents, stent-grafts, grafts and other endoluminal prostheses whether self-expanding, balloon expandable, self-expanding and balloon expandable or otherwise expandable as are known in the art.

In addition to the over-the-wire embodiments (example also found in U.S. Pat. No. 5,980,533) shown in FIGS. 1–4, the inventive catheter system may also be provided in a rapid-exchange configuration. Examples of rapid-exchange catheters may be found in U.S. Pat. Nos. 5,534,007 and 5,833,706. The inventive stent delivery systems may also be made in fixed wire form. Examples of fixed-wire catheters may be found in U.S. Pat. No. 5,702,364.

The system may be adapted for use with a medical device such as a stent, for example, a self-expanding, balloon expandable or combination self-expanding and balloon expandable stent. The system may also be used for delivery of other medical devices for use in the body as well including, but not limited to, ultrasonic devices, laser devices, vena cava filters, implantable drug delivery devices and the like.

The inventive medical systems disclosed herein may also be provided with any of the features disclosed in U.S. Pat. Nos. 6,096,056, 6,068,634, 6,036,697, 6,007,543, 5,968,069, 5,957,930, 5,944,726 , 5,653,691 and 5,534,007.

The stent delivery system may also comprise various coatings as are known in the art, including lubricious coatings to facilitate movement of the various parts of the system, as well as collagen-type coatings. More information concerning suitable coatings may be found in U.S. Pat. No. 5,443,907, and U.S. application Ser. Nos. 08/382478, 09/306939 and 09/316502.

The invention is also directed to medical device delivery systems and catheters produced using the inventive methods.

For the purposes of the detailed description of the invention, Figures of a portion of the distal end of a typical balloon catheter will be used. It should be understood, as mentioned above, that the present invention is applicable to other medical devices which include an expandable balloon. It should also be understood that the materials used may be any of those materials known in the art where applicable.

The illustrative figures show differing embodiments of the invention. Each balloon has proximal 12 and distal 14 waists, proximal 16 and distal 18 cone portions and a body 20 separating said waists and cones. In the cut away figures, an inner shaft 22 (guide wire shaft), marker bands 24, distal tip 26, outer shaft 28, guide catheter 30 and a guide wire 31 may be seen. These elements are well known in the art and serve as a framework to illustrate the balloon embodiments. The balloons may be considered deflated or partially inflated to illustrate the unique features of the balloon embodiments.

Balloons of the disclosed embodiments may be made of any suitable balloon material including compliant and non-compliant materials and combinations thereof. Compliant materials include low pressure, relatively soft or flexible polymeric materials, such as thermoplastic polymers, thermoplastic elastomers, polyethylene (high density, low density, intermediate density, linear low density), various co-polymers and blends of polyethylene, ionomers, polyesters, polyurethanes, polycarbonates, polyamides, poly-vinyl chloride, acrylonitrile-butadiene-styrene copolymers, polyether-polyester copolymers, and polyether-polyamide copolymers. Suitable materials include a copolymer polyolefin material available from E. I. DuPont de Nemours and Co. (Wilmington, Del.), under the trade name Surlyn™ Ionomer and a polyether block amide available under the trade name PEBAX™. Non-compliant materials include relatively rigid of stiff high pressure polymeric materials, such as thermoplastic polymers and thermoset polymeric materials, poly(ethylene terephthalate) (commonly referred to as PET), polyimide, thermoplastic polyamide, polyamides, polyesters, polycarbonates, polyphenylene sulfides, polypropylene and rigid polyurethane. Further examples of balloon material may be found in U.S. Pat. No. 6,146,356. It should be understood that the specific materials disclosed below for the individual embodiments does not limit the embodiment to those materials.

FIG. 1 shows balloon 10 having a body 20 which has a wavy configuration. A stent 21 is mounted on the balloon. Although the remaining figures do not show a stent, it should be understood that each embodiment may similarly have a stent mounted thereon. The wavy body 20 has a plurality of peaks 32 and troughs 34 which form the hinge points, as discussed above, to provide longitudinal flexibility in the balloon. In this particular embodiment, the entire body 20 wall is wavy, forming peaks and troughs from the outside of the balloon as well as from the inside of the balloon. The favored compliance of the balloon is also not distinctly altered.

The embodiments of the present invention improves flexibility and also provides for low compliance. Suitably, the balloons are semi-compliant or less.

The wavy nature of the balloon 10 also aids in stent 21 retention. The peaks 32 provide for an nonuniform surface which complements the nonuniform surface of a typical stent, therefore providing for greater friction and a more secure seat for the stent. The increased retention limits the axial movement of the stent during delivery and deployment.

It should also be understood that the embodiment is not limited to the full body 20 of the balloon being "wavy". Specific portions of the body 20 may comprise waves while the remaining portions of the balloon remain unchanged. For example, a portion in the middle of the body 20 may be wavy or a proximal and/or distal portion of the body 20 may be wavy, or combinations thereof. The body 20 may be tailored to the user's desires.

Figure 2:
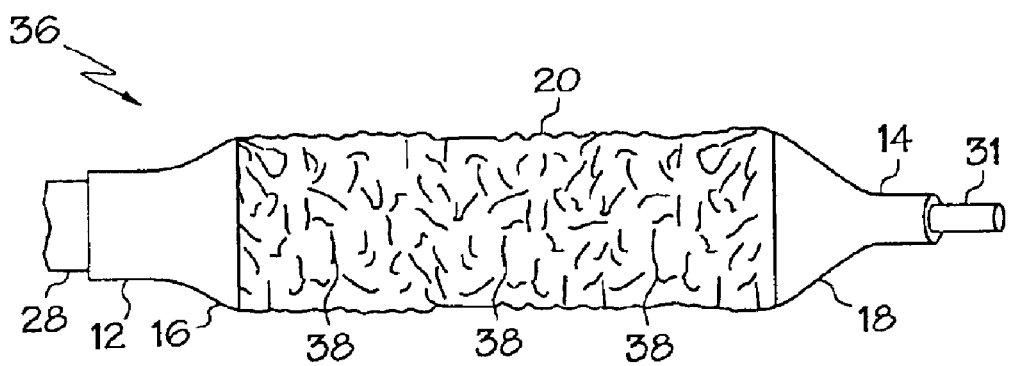
FIG. 2 is a side view of the distal end of a balloon catheter illustrating a particular embodiment of the inventive balloon.

FIG. 2 shows balloon 36 having a body 20 which has a wrinkled configuration. The wrinkled body 20 has a plurality of wrinkles 38 which form the hinge points, as discussed above, to provide longitudinal flexibility in the balloon. In this particular embodiment, the entire body 20 wall is wrinkled, forming a multitude of wrinkles 38 from the outside of the balloon as well as from the inside of the balloon. The favored compliance of the balloon is also not distinctly altered.

The wrinkled nature of the balloon 36 also aids in stent (not shown) retention. The wrinkles 38 provide for an nonuniform surface which complements the nonuniform surface of a typical stent, therefore providing for greater friction and a more secure seat for the stent. The increased retention limits the axial movement of the stent during delivery and deployment.

It should also be understood that the embodiment is not limited to the full body 20 of the balloon being "wrinkled". Specific portions of the body 20 may comprise wrinkles while the remaining portions of the balloon remain unchanged. For example, a portion in the middle of the body 20 may be wrinkled or a proximal and/or distal portion of the body 20 may be wrinkled, or combinations thereof. The body 20 may be tailored to the user's desires.

In one aspect, the "wrinkling" can be implemented as a process after molding the balloon. It can be compressed and expanded longitudinally multiple times to create the wrinkles. The wrinkle pattern can also be put into the balloon mold so that the molded pattern takes on the wrinkled pattern.

Figure 3:
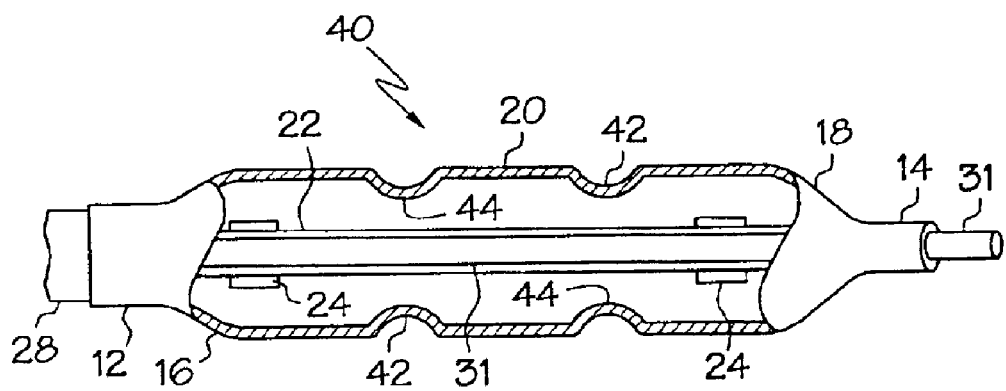
FIG. 3 is a partial cross-sectional view of the distal end of a balloon catheter illustrating a particular embodiment of the inventive balloon.

FIG. 3 shows balloon 40 having a body 20 which has two circumferential channels 42. A cross section of the balloon is shown to illustrate the balloon wall. The body 20 may have one or more channels 42 which form the hinge points, as discussed above, to provide longitudinal flexibility in the balloon. In this particular embodiment, the body 20 wall forms the channel such that the surface on the inside of the balloons forms an inward bulge 44. The favored compliance of the balloon is also not distinctly altered.

The channels 42 of the balloon 40 also aid in stent (not shown) retention. The channels 42 provide for an nonuniform surface which complements the nonuniform surface of a typical stent, therefore providing for greater friction and a more secure seat for the stent. The increased retention limits the axial movement of the stent during delivery and deployment.

It should also be understood that the embodiment is not limited to a specific number of channels 42. Specific portions of the body 20 may have channels while the remaining portions of the balloon remain unchanged. For example, a portion in the middle of the body 20 may have a channel or a proximal and/or distal portion of the body 20 may have channels, or combinations thereof. The body 20 may be tailored to the user's desires.

Figure 4:
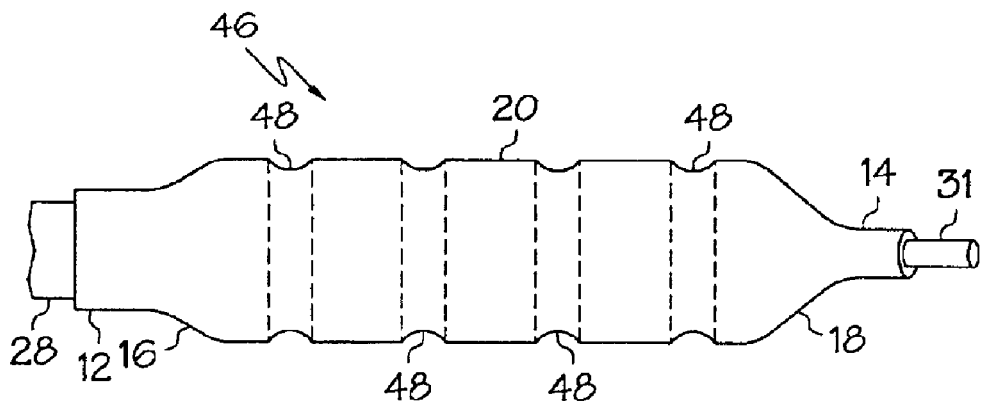
FIG. 4 is a side view of the distal end of a balloon catheter illustrating a particular embodiment of the inventive balloon.

FIG. 4 shows balloon 46 having a body 20 with ground rings. The body 20 has a plurality of ground rings 48 which form the hinge points, as discussed above, to provide longitudinal flexibility in the balloon. In this particular embodiment, the material of the body 20 wall is selectively ground to form rings. The resulting body wall 20 has less material in the ground ring 48 area, leaving the inside surface 50 of the balloon unchanged. This can be seen in FIG. 5 where a cross-section of the balloon 46 is revealed. The favored compliance of the balloon is also not distinctly altered.

Grinding, in this and any of the other embodiments requiring grinding, may be accomplished via conventional means, which include, but are not limited to, mechanical grinding or laser grinding. Examples of grinding may be seen in U.S. Pat. No. 6,193,738.

The ground nature of the balloon 46 also aids in stent (not shown) retention. The ground rings 48 provide for an nonuniform surface which complements the nonuniform surface of a typical stent, therefore providing for greater friction and a more secure seat for the stent. The increased retention limits the axial movement of the stent during delivery and deployment.

It should also be understood that the embodiment is not limited to the number or positioning of the ground rings 48. Specific portions of the body 20 may comprise ground rings 48 while the remaining portions of the balloon remain unchanged. For example, there may be a ring or rings in the middle or on the proximal and/or distal portion of the body 20, or combinations thereof. The body 20 may be tailored to the user's desires.

The embodiment may be made using any conventional methods. Suitable methods may include centerless grinding of a balloon blank and laser cutting of a molded balloon.

Figure 5:
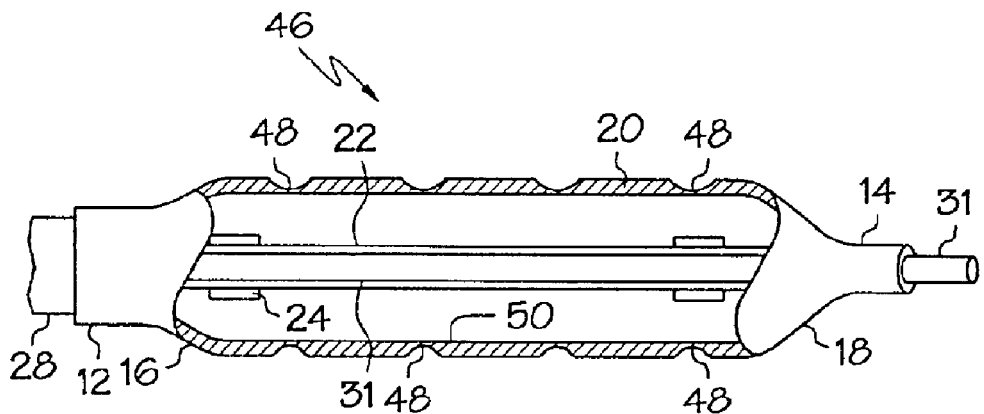
FIG. 5 is a partial cross-sectional view of the embodiment shown in FIG. 4.
Figure 6:
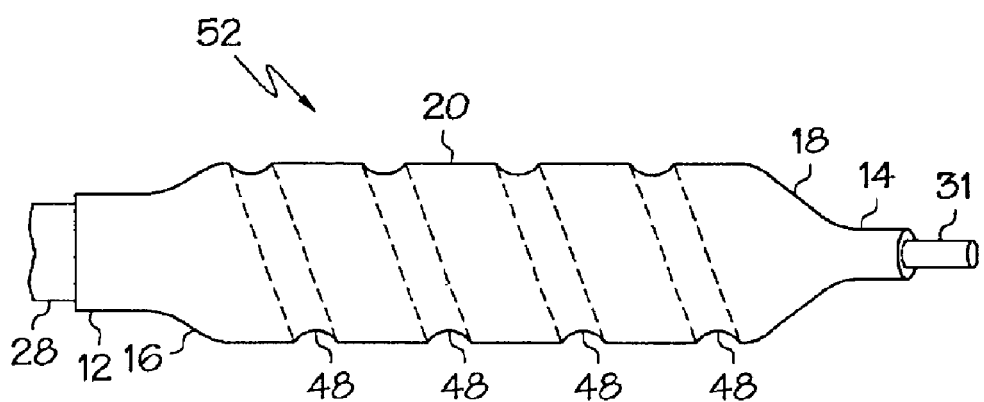
FIG. 6 is a side view of the distal end of a balloon catheter illustrating a particular embodiment of the inventive balloon.

FIG. 6 illustrates a balloon 52 which is a modification of the embodiment of FIGS. 4–5, wherein the ground rings 48 are in a spiral configuration. The rings 48 may take the form of one continuous spiral or separate rings 48 which are slanted relative to the axis of the catheter.

Figure 7:
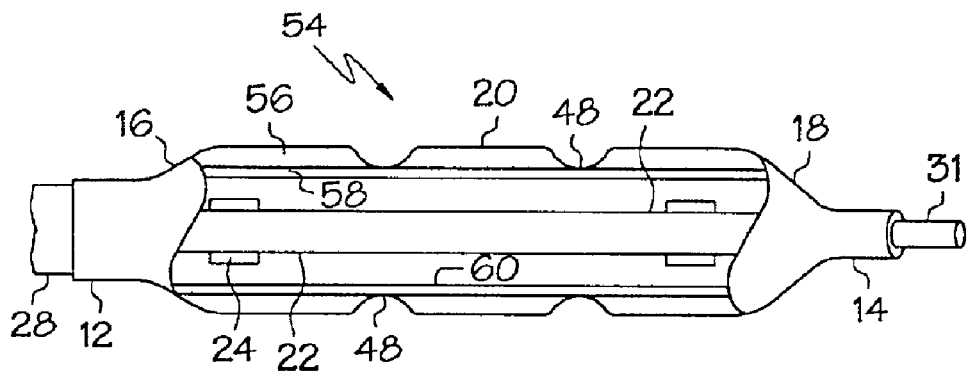
FIG. 7 is a partial cross-sectional view of the distal end of a balloon catheter illustrating a particular embodiment of the inventive balloon.

FIG. 7 shows balloon 54 having a body 20 with ground rings 48, as discussed above. However, in this embodiment, the body 20 wall is a co-extrusion. Co-extrusions are well-known in the art. The body 20 wall comprises a first layer 56 on the outside of the balloon body 20 and a second layer 58 on the inside of the balloon body 20.

As can be seen, the body 20 has a plurality of ground rings 48 which form the hinge points, as discussed above, to provide longitudinal flexibility in the balloon. In this particular embodiment, the material of the body 20 wall is selectively ground to form rings. The resulting body wall 20 has less material in the ground ring 48 area, leaving the inside surface 60 of the balloon unchanged. This can be seen in FIG. 7 where a cross-section of the balloon 46 is revealed. The favored compliance of the balloon is also not distinctly altered.

The embodiment of FIG. 7 allows for a deeper grind since there are two layers. This allows for greater longitudinal flexibility in the balloon wall. The depth of the grind can be dictated by the needs of the user, limited only by the thickness of the two layer body wall 20. Combination of grinding patterns may be employed. In FIG. 7, the ground ring extend through the first layer 56, but does not penetrate the second layer 58.

The two layers may comprise the same or different materials. Different materials allow the designer to alternate between hard and soft polymers to achieve better flexibility with low compliance. Suitable materials include, but are not limited to, thermoplastic elastomers, such as PEBAX, polyester-polyether block copolymers such as ARNITEL and HYTREL and polyurethane. Suitable combinations include, but are not limited to, PEBAX with Nylon (suitably nylon 12), ARNITEL with PBT or PET and Polyurethane with a polymer having a higher hardness or an aromatic polymer.

The ground nature of the balloon 46 also aids in stent (not shown) retention. The ground rings 48 provide for an nonuniform surface which complements the nonuniform surface of a typical stent, therefore providing for greater friction and a more secure seat for the stent. The increased retention limits the axial movement of the stent during delivery and deployment.

It should also be understood that the embodiment is not limited to the number or positioning of the ground rings 48. Specific portions of the body 20 may comprise ground rings 48 while the remaining portions of the balloon remain unchanged. For example, there may be a ring or rings in the middle or on the proximal and/or distal portion of the body 20, or combinations thereof. As with FIG. 6, the ground rings 48 may be in a spiral configuration. The rings 48 may take the form of one continuous spiral or separate rings 48 which are slanted relative to the axis of the catheter. The body 20 may be tailored to the user's desires.

It should be understood that the co-extrusion element of this embodiment may be incorporated into any of the other embodiments of the present application.

Figure 8:
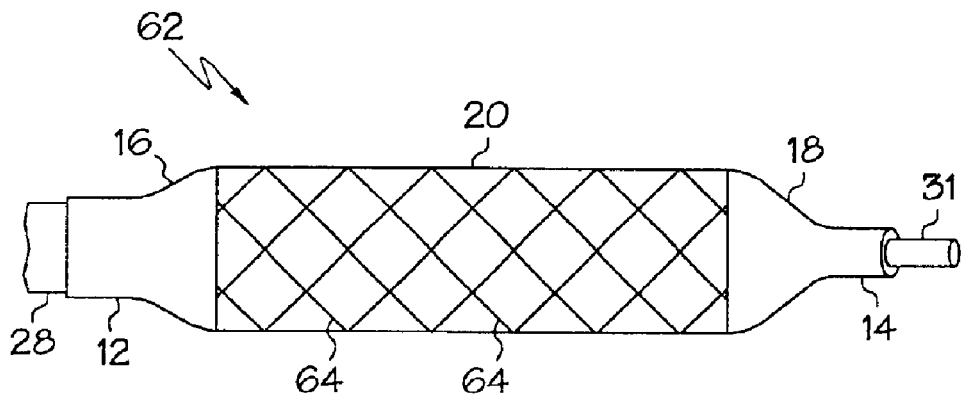
FIG. 8 is a side view of the distal end of a balloon catheter illustrating a particular embodiment of the inventive balloon.

FIG. 8 illustrates a balloon 62 body 20 incorporating a pattern of recesses or grooves 64 in a pattern which are cut or ground into the balloon 62 material. The process involves grinding from different directions. FIG. 8 illustrates what is commonly referred to as a quilt pattern, although other patterns may be used. The pattern is cut into the balloon material via conventional mechanical or laser methods. The grooves 64 form the hinge points, as discussed above, to provide longitudinal flexibility in the balloon. The favored compliance of the balloon is also not distinctly altered.

Patterns can be imparted to the balloons by forming the patterns on the inside of the mold in which the balloons are shaped. When the balloons are blown in the mold, the balloon takes on the pattern on the inside of the balloon. If the balloon mold has a quilted pattern, then a balloon molded in it will have a quilted pattern, etc.

The grooves 64 of the balloon 62 also aid in stent (not shown) retention. The grooves 64 provide for an nonuniform surface which complements the nonuniform surface of a typical stent, therefore providing for greater friction and a more secure seat for the stent. The increased retention limits the axial movement of the stent during delivery and deployment.

It should also be understood that the embodiment is not limited to a specific pattern of grooves 64. Specific portions of the body 20 may have grooves 64 while the remaining portions of the balloon remain unchanged. For example, a portion in the middle of the body 20 may have a grooves or a proximal and/or distal portion of the body 20 may have grooves, or combinations thereof. The body 20 may be tailored to the user's desires.

Figure 9:
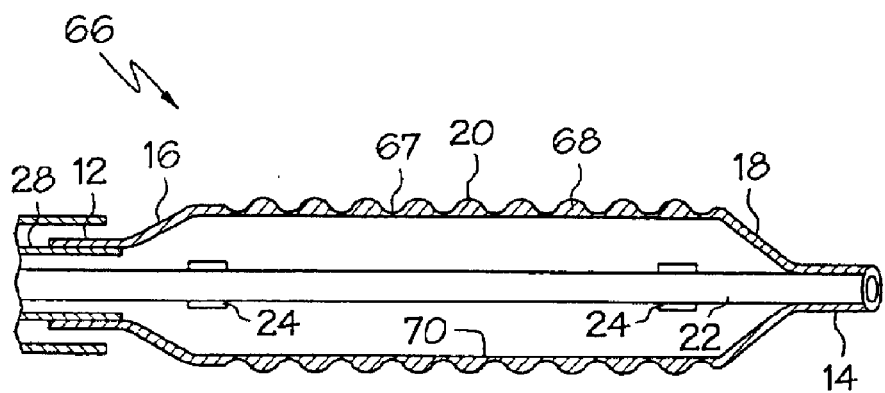
FIG. 9 is a cross-sectional view of the distal end of a balloon catheter illustrating a particular embodiment of the inventive balloon.

FIG. 9 shows balloon 66 having a body 20 with a plurality of thin portions 67 and a plurality of thick portions 68. The inside 70 of the body wall 20 has a relatively even contour as apposed to the undulating contour of the outer body wall. The body wall may comprise one hard material. Suitable materials include, but are not limited to, PET, nylon, polyethylene and hard polyurethanes. The cones and waists of the balloon may also have the altered contour.

As can be seen, the outside of body 20 has an undulating contour defining a plurality of thin portions 67 which form the hinge points, as discussed above, to provide longitudinal flexibility in the balloon. Suitably, the balloons are formed and then ground or thermo formed with the desired contour. The thin portions are achieved through mechanical or laser grinding of the balloon tube, after which the balloon is formed. The resulting body wall 20 has less material in the thin portions 67, leaving the inside surface 70 of the balloon unchanged. The thickness of the thin portions can be dictated by the needs of the user, limited only by the thickness of the body wall 20. The favored compliance of the balloon is also not distinctly altered.

The undulating nature of the balloon 66 also aids in stent (not shown) retention. The body 20 provides for an nonuniform surface which complements the nonuniform surface of a typical stent, therefore providing for greater friction and a more secure seat for the stent. The increased retention limits the axial movement of the stent during delivery and deployment.

It should also be understood that the embodiment is not limited to the number or positioning of the thin portions 67. Specific portions of the body 20 may comprise thin portions 67 while the remaining portions of the balloon remain unchanged. For example, there may be thin portions 67 in the middle or on the proximal and/or distal portion of the body 20, or combinations thereof. The thin portions 67 may be in a spiral configuration. The thin portions 67 may take the form of one continuous spiral or separate rings which are slanted relative to the axis of the catheter. The body 20 may be tailored to the user's desires.

The balloons of the present invention may also comprise plurality of materials to produce the hinge effects. These designs utilize two materials with different modulus of elasticity. The materials can be combined on and/or in a balloon in a way as to provide flexibility in the longitudinal direction and stiffness or non-compliance in the radial direction. For the remaining embodiments, the harder material is relatively non-compliant and the softer material is relatively compliant. Suitable harder materials include, but are not limited to, polyethyleneterephthalate (PET), and polybutylene terephthalate (PBT). Suitable softer materials include, but are not limited to, HYTREL®, which are randomized block co-polymers of polyethers and polyesters, and other thermoplastic elastomers. Other useful balloon materials have been listed above with regard to the previous embodiments, and are further listed below. It should be understood that the specific materials disclosed below for the individual embodiments does not limit the embodiment to those materials.

It should be understood that the two materials may be hard and soft, respectively, relative to each other. As such, the balloon may consist of two hard materials or two soft material, as long as one material is harder than the other.

Figure 10:
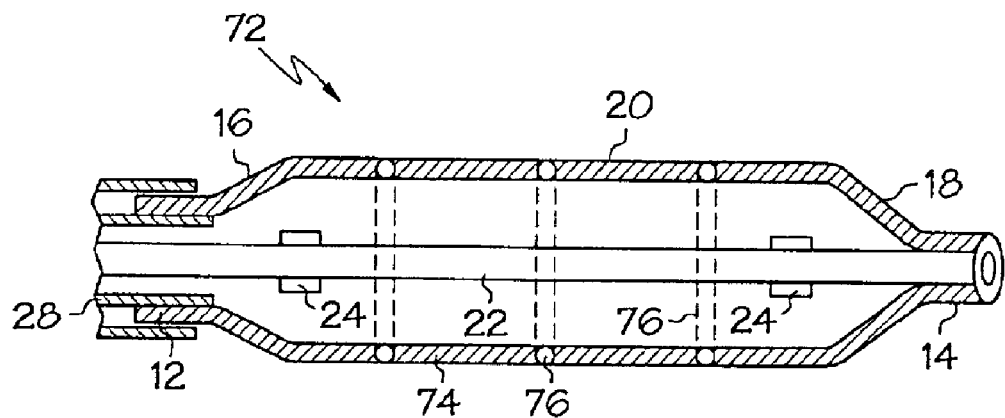
FIG. 10 is a cross-sectional view of the distal end of a balloon catheter illustrating a particular embodiment of the inventive balloon.
Figure 11:
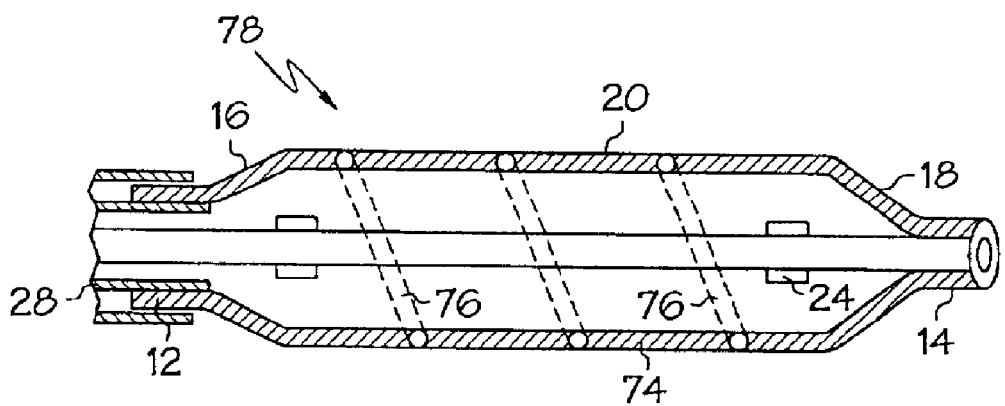
FIG. 11 is a cross-sectional view of the distal end of a balloon catheter illustrating a particular embodiment of the inventive balloon.

FIG. 10 shows balloon 72 having a body 20 with a plurality of rings 76 within the balloon material 74. In the embodiment shown, the rings 76 are continuous, however, it should be understood that the rings may be discontinuous, but generally forming a ring. Only the continuous rings are shown. These embodiments illustrate the use of at least two materials varying in hardness. Suitably, the difference is at 10 Shore D or larger. The embodiments shown in FIGS. 10–11 have a plurality of soft rings 76 incorporated within the harder body material 74. The soft rings 76 which interrupt the harder body material 74 act as hinge points for longitudinal flexibility without sacrificing radial extension.

In this particular embodiment, the rings 74 are incorporated within the body wall 20. The inside and outside surfaces of the body wall 20 are relatively uninterrupted and have relatively smooth contours. However, the rings 76 may protrude from the surface of the body wall 20 either on the inside or the outside, or both.

It should also be understood that the embodiment is not limited to the number or positioning of the soft rings 76. Specific portions of the body 20 may comprise soft rings 76 while the remaining portions of the balloon remain unchanged. For example, there may be soft rings 76 in the middle or on the proximal and/or distal portion of the body 20, or combinations thereof. The soft rings 76 may be in a spiral configuration as shown in balloon 78 in FIG. 11. The soft rings 76 may take the form of one continuous spiral or separate rings which are slanted relative to the axis of the catheter. The body 20 may be tailored to the user's desires.

Figure 12:
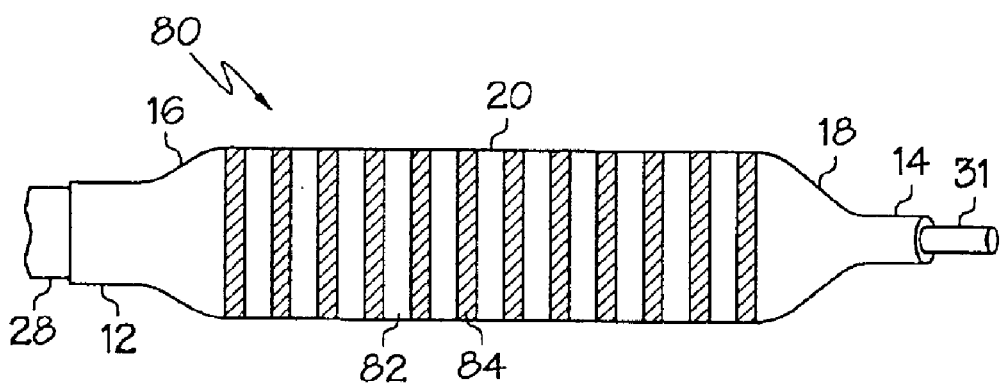
FIG. 12 is a side view of the distal end of a balloon catheter illustrating a particular embodiment of the inventive balloon.

FIG. 12 shows balloon 80 having a body 20 with a plurality of rings 84 within the balloon material 82. In the embodiment shown, the rings 84 are continuous, however, it should be understood that the rings may be discontinuous, but generally forming a ring. Only the continuous rings are shown.

These embodiments also illustrate the use of at least two materials varying in hardness. As above, suitably, the difference is at 10 Shore D or larger. The embodiments shown in FIG. 12 have a plurality of hard rings 84 incorporated within the softer body material 82. The softer body material 82 between the hardened rings 84 act as hinge points for longitudinal flexibility without sacrificing radial extension. The hardened rings 84 prevent growth in the radial direction while the softer sections between the hardened rings 84 provide longitudinal flexibility.

In this particular embodiment, the rings 84 are incorporated within the body wall 20. The inside and outside surfaces of the body wall 20 are relatively uninterrupted and have relatively smooth contours. However, the rings 84 may protrude from the surface of the body wall 20 either on the inside or the outside, or both. The rings may also help with stent securement.

It should also be understood that the embodiment is not limited to the number or positioning of the hardened rings 84. Specific portions of the body 20 may comprise hardened rings 84 while the remaining portions of the balloon remain unchanged. For example, there may be hardened rings 84 in the middle or on the proximal and/or distal portion of the body 20, or combinations thereof. The hardened rings 84 may be in a spiral configuration. The hardened rings 84 may take the form of one continuous spiral or separate rings which are slanted relative to the axis of the catheter. The body 20 may be tailored to the user's desires.

Figure 13:
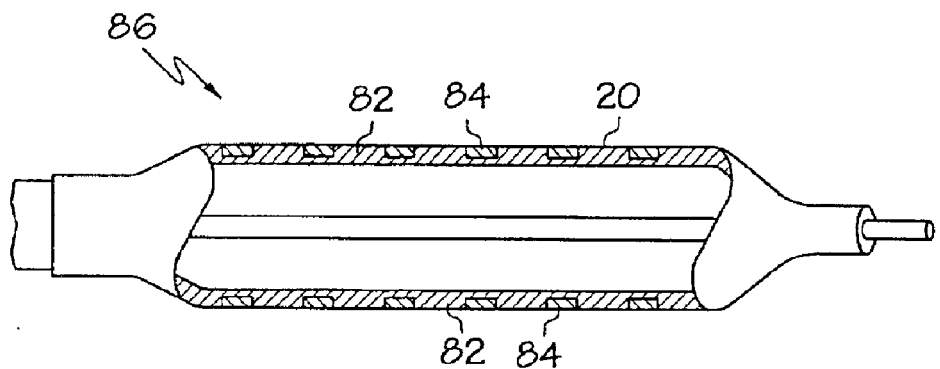
FIG. 13 is a partial cross-sectional view of the distal end of a balloon catheter illustrating a particular embodiment of the inventive balloon.
Figure 14:
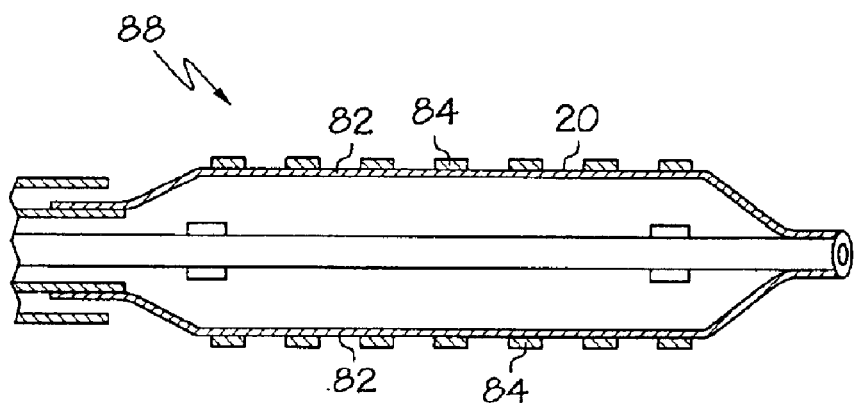
FIG. 14 is a cross-sectional view of the distal end of a balloon catheter illustrating a particular embodiment of the inventive balloon.
Figure 15:
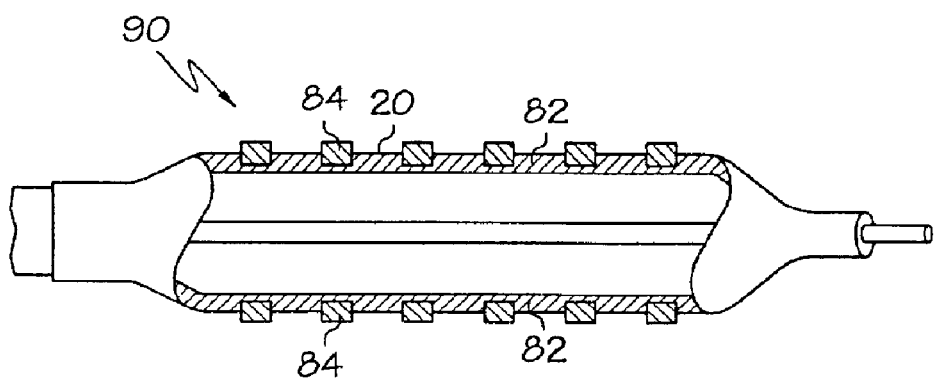
FIG. 15 is a partial cross-sectional view of the distal end of a balloon catheter illustrating a particular embodiment of the inventive balloon.

FIGS. 13–15 are variations of the embodiment of FIG. 12. The figures show varying positions of the hardened rings 84. Balloon 86 of FIG. 13 shows the hardened rings 84 embedded within the softer material 82 of the balloon wall 20 such the contour of the outside of the balloon body wall 20 is relatively smooth. The hardened rings 84 do not however extend the width of the body wall 20.

Balloon 88 of FIG. 14 shows the hardened rings 84 on the surface of the softer material 82 of the balloon wall 20 such that the contour of the outside of the balloon body wall 20 is uneven or bumpy. As discussed above, the uneven contour aids in the retention of a stent.

Balloon 90 of FIG. 15 is a combination of balloons 86 and 88. Balloon 90 shows the hardened rings 84 embedded within the softer material 82 of the balloon wall 20. The hardened rings 84 do not however extend the width of the body wall 20. The hardened rings 84 do however extend above the surface of the softer material 82, such that the contour of the outside of the balloon body wall 20 is uneven or bumpy. As discussed above, the uneven contour aids in the retention of a stent.

Suitable materials include, but are not limited to, thermoplastic elastomers, such as PEBAX, polyester-polyether block copolymers such as ARNITEL and HYTREL and polyurethane. Suitable materials are also included in U.S. Pat. No. 6,146,3356 in addition to materials mentioned above. Suitable combinations include, but are not limited to, PEBAX with Nylon (suitably nylon 12), ARNITEL with PBT or PET and Polyurethane with a polymer having a higher hardness or an aromatic polymer.

Based on the above description it should be understood that several different polymers with a wide range of characteristics may be used to form a longitudinal or longitudinal and radial stabilized balloon of the present invention.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each single dependent claim format which creates a dependency from a prior antecedent-possessing claim other than the specific claim listed in such dependent claim below (e.g. claim 6 may be taken as alternatively dependent from any of claims 2–5, claim 4 may be taken as alternatively dependent from claim 3; etc.).

What is claimed is:

1. A balloon for a medical device comprising:

a longitudinal axis;

a proximal cone and a distal cone; and a body positioned between the proximal and distal cones, the body comprising a body wall, the body wall forming closed loop around the longitudinal axis and the body wall having a thickness, the body wall further comprising an inner wall and an outer wall, wherein the body wall comprises a plurality of hinge points around the longitudinal axis of the balloon, wherein the plurality of hinge points comprises at least two circumferential channels formed in the outer wall of the body wall, the at least two circumferential channels each being a circumferential thinning of the body wall and constituting a minority of the body wall, wherein the majority of the body wall is thicker than the at least two circumferential channels, the plurality of hinge points providing the body with increased longitudinal flexibility.

2. The balloon of claim 1, wherein the body wall has a wavy configuration forming a plurality of peaks and troughs, the peaks and trough forming the plurality of hinge points providing the increased longitudinal flexibility.

3. The balloon of claim 1, wherein the plurality of hinge points are wrinkles dispersed throughout the body wall.

4. The balloon of claim 1, wherein the circumferential channels are ground into the body wall such that the inner wall has a substantially uninterrupted contour.

5. The ballon of claim 4, wherein the circumferential channels are in a spiral configuration relative to the axis of the body.

6. The balloon of claim 4, wherein the circumferential channels are on a bias relative to the axis of the body.

7. The balloon of claim 4, the body wall being a coextrusion such that the body wall comprises a first layer and a second layer.

8. The balloon of claim 7, wherein the first layer has separations along is length and the second layer is substantially continuous along its length.

9. The balloon of claim 1, wherein the circumferential channels are in a spiral configuration relative to the axis of the body.

10. The balloon of claim 1, wherein the circumferential channels are on a bias relative to the axis of the body.

11. The balloon of claim 1, wherein the plurality of hinge points are grooves in the body wall material.

12. The balloon of claim 11, wherein the grooves form a quilted pattern.

13. The balloon of claim 1, wherein the thickness of the body wall varies along the axis of the body forming a plurality of first portions interspersed with a plurality of second portion, the first portions being thinner than the second portions.

14. The balloon of claim 1, wherein the outer surface has an undulating contour and the inner surface has a substantially continuous contour.

15. The balloon of claim 13, wherein the body wall comprises hard material.

16. The balloon of claim 1, further comprising a stent crimped on the balloon, wherein the plurality of hinge points improve the securement of the stent on the balloon relative to a balloon without the plurality of hinge points.

* * * * *